(12) United States Patent
Hong

(10) Patent No.: US 7,081,259 B2
(45) Date of Patent: Jul. 25, 2006

(54) HERBAL, EXTRACT HAVING THERAPEUTIC ACTIVITY ON INJURIES, AND PHARMACEUTICAL COMPOSITION AND HEALTH FOOD CONTAINING THE SAME

(75) Inventor: Jong-Soo Hong, Shindongah Apt. #113-202, 366, Joonggye-dong, Nowon-ku, 139-220, Seoul (KR)

(73) Assignees: Healthy & Happy Co., Ltd. (KR); Jong-Soo Hong (KR)

( * ) Notice: Subject to any disclaimer, the term of this patent is extended or adjusted under 35 U.S.C. 154(b) by 0 days.

(21) Appl. No.: 10/468,421

(22) PCT Filed: Feb. 20, 2002

(86) PCT No.: PCT/KR02/00266

§ 371 (c)(1),
(2), (4) Date: Aug. 18, 2003

(87) PCT Pub. No.: WO02/066042

PCT Pub. Date: Aug. 29, 2002

(65) Prior Publication Data

US 2004/0076689 A1 Apr. 22, 2004

(30) Foreign Application Priority Data

Feb. 20, 2001 (KR) .................. 2001-8383

(51) Int. Cl.
*A61K 36/25* (2006.01)
(52) U.S. Cl. ............. 424/728; 424/739; 424/748; 424/756; 424/757; 424/771; 424/773; 424/775; 424/776; 424/777; 424/778
(58) Field of Classification Search ............... 424/725, 424/728, 739, 748, 756, 757, 771, 773, 775, 424/776, 777, 778
See application file for complete search history.

(56) References Cited

U.S. PATENT DOCUMENTS 4,456,597 A * 6/1984 Kojima et al.
4,613,591 A * 9/1986 Aburada et al.
5,876,728 A * 3/1999 Kass et al.

FOREIGN PATENT DOCUMENTS

JP 07-258104 * 10/1995

OTHER PUBLICATIONS

CAPLUS English abstract of Kim et al. Yakhak Hoechi (2000), vol. 44, No. 3, pp. 283-292.*
DERWENT English abstract of CN 1166923 A (1997).*
DERWENT English abstract of CN 1139565 A (1997).*
English abstract of JP 402300131 A (1990).*
CAPLUS English abstract of KR 2000066374 A (2000).*

* cited by examiner

Primary Examiner—Susan D. Coe
(74) Attorney, Agent, or Firm—Peter F. Corless; Christine C. O'Day; Edwards Angell Palmer & Dodge LLP

(57) ABSTRACT

The present invention relates to an extract having healing activity on injuries, which is obtained by extracting Astragali Radix, Ginseng Radix, Carthami Flos, Angelicae Gigantis Radix, Cnidii Rhizoma, Rehmanniae Radix Preparata, Paeoniae Radix and Cinnamomi Cortex Spissus with water while heating, and a pharmaceutical composition for treating injuries, a health food for post-surgical recovery and an animal feed containing said extract as the active ingredient.

10 Claims, 16 Drawing Sheets

HERBAL, EXTRACT HAVING THERAPEUTIC ACTIVITY ON INJURIES, AND PHARMACEUTICAL COMPOSITION AND HEALTH FOOD CONTAINING THE SAME

TECHNICAL FIELD

The present invention relates to a herbal extract composition having healing activity for injuries, and, more specifically, to the extract composition obtained by extracting Astragali Radix, Ginseng Radix, Carthami Flos, Angelicae Gigantis Radix, Cnidii Rhizoma, Rehmanniae Radix Preparata, Paeoniae Radix, and Cinnamomi Cortex Spissus with water while heating, and to a pharmaceutical composition for healing injuries, and a health food and an animal feed for post-surgical recovery containing said extract as the active ingredient.

BACKGROUND ART

Bones, flesh, etc. are hurt by injuries, for example, punctured wound, laceration, wound or fracture, or surgical operations. Many studies on methods to heal the injuries and to repair the bones and flesh have been continuously made, and thus, a number of healing methods and agents are known in the Oriental and Western Medicines at the present time.

In the Western medicine, surgical operation techniques have more advanced than in the Oriental medicine. Healing agents administered after injuries or surgeries, however, do not have very good effects and have the problem to cause many side effects. For this reason, despite administering several wound- or fracture-healing agents to patients with injuries or surgeries, it is frequently shown that injuries are not well healed up, patients are weakened or suffered from severe pain, suture of fractured bone is delayed, and side effects like gastric disorders from healing agents, e.g. anti-inflammatory drugs, are accompanied.

In contrast, according to the Chinese medicine, if human beings, who live by Qi-blood-essence of life-vitality, are injured on bones or flesh, skin, subcutaneous fatty layer, flesh and muscle are regenerated, and bones, bone marrow and brain are replenished, and stagnated blood is replaced with fresh blood, by making Qi-blood-essence of life-vitality higher and eliminating extravasated blood to promote vital essence and energy. Based on this theory, various kinds of healing methods and agents are handed down in the Chinese medical literature. However, it has been difficult to get satisfactory effects only by such traditional prescriptions.

DISCLOSURE OF THE INVENTION

The present inventors referred to many Chinese medical literature handed down from ancient times, and conducted many studies and experiments to develop a healing agent for various injuries, particularly wounds, fractures, etc., or health food for post-surgical recovery. As a result, the inventors found that a suitable combination of specific herbal medicines has excellent healing effects on injuries compared with other known agents without any toxicity and side effect, and completed the present invention.

The present invention relates to an extract composition having healing activity for injuries, which is obtained by extracting Astragali Radix, Ginseng Radix, Carthami Flos, Angelicae Gigantis Radix, Cnidii Rhizoma, Rehmanniae Radix Preparata, Paeoniae Radix and Cinnamomi Cortex Spissus with water while heating.

The extract composition of the present invention exhibits healing activity from the above-described herbal medicines for injuries, but to strengthen its activity, one or more selected from the group consisting of Atractylodis Rhizoma alba, Hoelen, Aurantii Nobilis Pericarpium, Glycyrrhizae Radix, Eucommiae Cortex, Myrrh, Amomi Semen, Walnut, Zingiberis Rhizoma and Zizyphi Fructus are further mixed and the whole mixture is extracted with water while heating.

As raw herbal medicines essential for the present invention, Astragali Radix has Qi-replenishing, pus-evacuating by administering tonics, and pain-arresting activities; Ginseng Radix has tonic, stamina-strengthening, calming and fatigue-relieving activities; Carthami Flos enhances functions of bone tissue cells to promote growth of bones; Angclicae Gigantis Radix has blood-replenishing, moistening, calming, analgesic and antibacterial activities; Cnidii Rhizoma has blood- and Qi-promoting activities; Rehmanniae Radix Preparata has blood-replenishing, tonic and nourishing activities; Paeoniae Radix has calming, antispasmodic, antipyretic, analgesic, antibacterial, anti-inflammatory and vasodilating activities; and Cinnamomi Cortex Spissus has analgesic and antispasmodic activities.

As raw herbal medicines which can be further added for the present invention, Atractylodis Rhizoma alba has spleen-tonifying and Qi-replenishing, dampness-eliminating and diuresis-inducing, and exterior-reinforcing and sweating-suppressing activities; Hoelen has stomachic, diuretic and calming activities; Aurantii Nobilis Pericarpium has Qi-flow-regulating and spleen-tonifying, stagnation of Qi-removing and phlegni-eliminating, and antiasthmatic and cough-relieving activities; Glycyrrhizae Radix has cough-relieving, phlegm-eliminating, detoxifying, antispasmodic, anti-inflammatory, analgesic, and anti-hypersensitive activities; Eucornmiae Cortex has tonic, stamina-strengthening, and analgesic activities; Myrrh has blood-circulation-promoting and pain-arresting activities, and swelling-inducing and Qi-vitalizing activities; Amomi Semen has spleen-tonifying and Qi-promoting, and spleen-warming and antidiarrheal activities; Walnut has kidney reinforcing and muscle-and-bone-strengthening activities; Zingiberis Rhizoma has a stomachic activity; and Zizyphi Fructus has tonic, blood-replenishing, laxative, calming, and analgesic activities.

The composition of the present invention may be preferably obtained by extracting 4–20 parts of Astragali Radix, 2–12 parts of Ginseng Radix, 2–12 parts of Carthami Flos, 2–12 parts of Angelicae Gigantis Radix, 2–12 parts of Cnidii Rhizoma, 2–12 parts of Rehmanniae Radix Preparata, 2–12 parts of Paeoniae Radix, and 2–12 parts of Cinnamomi Cortex Spissus, wherein all the above parts are based on weights of raw herbal medicines, with water while heating. More preferably, the composition is prepared from 8–16 parts of Astragali Radix, 4–8 parts of Ginseng Radix, 4–8 parts of Carthami Flos, 4–8 parts of Angelicae Gigantis Radix, 4–8 parts of Cnidii Rhizoma, 4–8 parts of Rehmanniae Radix Preparata, 4–8 parts of Paeoniae Radix, and 4–8 parts of Cinnamomi Cortex Spissus, wherein all the above parts are based on weights of raw herbal medicines.

Also, the composition of the present invention is preferably prepared by further mixing 2–12 parts of Atractylodis Rhizoma alba, 2–12 parts of Hoelen, 2–10 parts of Aurantii Nobilis Pericarpium, 2–12 parts of Glycyrrhizae Radix, 2–18 parts of Eucommiae Cortex, 2–8 parts of Myrrh, 2–12 parts of Amomi Semen, 4–20 parts of Walnut, 2–10 parts of Zingiberis Rhizoma, and 2–10 parts of Zizyphi Fructus, wherein all the above parts are based on weights of raw herbal medicines, and extracting the whole mixture with water while heating. More preferably, the composition is prepared by further mixing 4–8 parts of Atractylodis Rhizoma alba, 4–8 parts of Hoelen, 3–8 parts of Aurantii Nobilis Pericarpium, 4–8 parts of Glycyrrhizae Radix, 4–10 parts of Eucommiae Cortex, 2–6 parts of Myrrh, 4–8 parts of Amomi Semen, 6–15 parts of Walnut, 3–8 parts of Zingiberis Rhizoma, and 3–8 parts of Zizyphi Fructus, wherein all the above parts are based on weights of raw herbal medicines.

The above composition ratios of the herbal medicines are based on the results of many times of clinical and animal experiments, and, if lower than the lower limits, pharmacological effects of the ingredients are remarkably decreased, and, if higher than the upper limits, pharmacological effects of other ingredients are decreased to remarkably deteriorate synergistic and cooperative effects of the composition.

As shown in the following Experiments 1 and 2, the herbal extract composition prepared by the above-described method, has healing activity for injuries, particularly, wounds or fracture. Therefore, the extract composition of the present invention can be used as a healing agent for injuries such as wounds or fractures, or as a health food or an animal feed for post-surgical recovery of human beings or animals.

Therefore, the present invention provides a pharmaceutical composition for healing injuries in human beings or animals comprising the above extract composition as the active ingredient. Also, the present invention provides a health food or an animal feed for post-surgical recovery of human beings or animals comprising the above extract composition as the active ingredient.

The composition of the present invention may be prepared in the form of solution, suspension, pill, tablet, capsule or granule by combining the extract composition obtained by extracting the mixture of the above herbal medicines with water while heating, a mixture of the extract obtained by extracting each herbal medicine with a solvent depending upon its physicochemical properties, or powder obtained by concentrating and drying the extract, with pharmaceutically acceptable carriers, according to conventional methods. The composition is preferably prepared in the form of oral solution, suspension or tablet, for good pharmacological effects, but, if necessary, may be prepared in the form of pill, capsule or granule, and, if necessary, may be changed into another dosage form before its use.

For example, the pharmaceutical composition of the present invention is prepared by pouring 300 ml of water into the mixture of 4–20 g of Astragali Radix, 2–12 g of Ginseng Radix, 2–12 g of Carthami Flos, 2–12 g of Angelicae Gigantis Radix, 2–12 g of Cnidii Rhizoma, 2–12 g of Rehmanniae Radix Preparata, 2–12 g of Paeoniae Radix and 2–12 g of Cinnamomi Cortex Spissus, and optionally, one or more selected from the groups consisting of 2–12 g of Atractylodis Rhizoma alba, 2–12 g of Hoelen, 2–10 g of Aurantii Nobilis Pericarpium, 2–12 g of Glycyrrhizae Radix, 2–18 g of Eucommiae Cortex, 2–8 g of Myrrh, 2–12 g of Amomi Semen, 4–20 g of Walnut, 2–10 g of Zingiberis Rhizoma, and 2–10 g of Zizyphi Fructus, extracting the whole mixture while heating for about 2 hours, filtering the extract, and concentrating the filtrate to 120 ml or freeze-drying it.

A single dose of the present composition is usually in the range of 0.1 to 30 g as freeze-dried powder for an adult, and it is taken once to three times a day. However, a dosage of the composition of the present invention may be suitably changed depending upon a patient's body weight, age, sexuality, severity of disease, and digestibility. Other formulations may also be taken at suitable dosages.

BEST MODE FOR CARRYING OUT THE INVENTION

Hereinafter, this invention will be more specifically explained with reference to examples, but they should not be construed to limit the present invention in any manner.

EXAMPLE 1

Preparation of Solution and Freeze-dried Powder

Into a mixture of 80 g of Astragali Radix, 60 g of Ginseng Radix, 60 g of Carthami Flos, 50 g of Angelicae Gigantis Radix, 50 g of Cnidii Rhizoma, 50 g of Rehmanniae Radix Preparata, 50 g of Paeoniae Radix, 50 g of Cinnamomi Cortex Spissus, 50 g of Atractylodis Rhizoma alba, 50 g of Hoelen, 50 g of Aurantii Nobilis Pericarpium, 60 g of Glycyrrhizae Radix, 60 g of Eucommiae Cortex, 20 g of Myrrh, 40 g of Amomi Semen, 60 g of Walnut, 40 g of Zingiberis Rhizoma, and 40 g of Zizyphi Fructus was poured 2000 ml of water. The whole mixture was extracted while heating for about 2 hours and filtered, and then, the filtrate was concentrated to 900 ml. Then, the concentrate was freeze-dried to obtain 110 g of the powdered extract.

EXAMPLE 2

Preparation of Other Formulations

According to conventional methods, pills, granules, sprays, tablets, and capsules were prepared using the extract composition or its concentrated dried powder obtained from the above Example 1.

EXPERIMENT 1

Evaluation of Wound-healing Effect

The composition of the present invention, which was orally administered, was tested for its healing effect on full-thickness skin wound induced in the dorsal area of rats.

Three square skin wounds, each of which had the size of 1 cm×1 cm, were induced in the dorsal side of fifteen male rats with the age of 10 weeks.

For trial groups, the composition obtained from the above Example 1 was orally administered to the rats at 200 mg/kg body weight (high-dosage group), 50 mg/kg body weight (low-dosage group), and 0 mg/kg body weight (control group) once a day for 14 days, respectively, and degrees of contraction, re-epithelialization, and healing of wound were histopathologically examined with the naked eyes.

Figure 1:
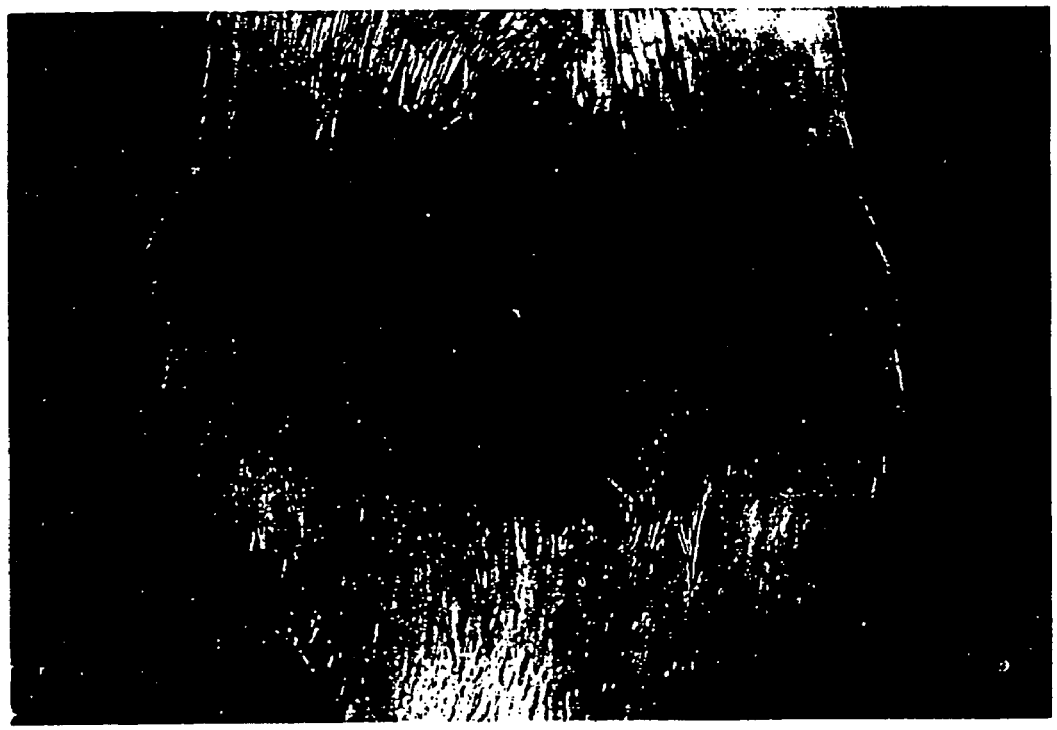
FIG. 1 is a photograph of a rat in which skin wounds are induced.
Figure 2:
FIGS. 2 to 7 are photographs showing the wounded sites after orally administering 0 mg/kg (control), 50 mg/kg (low-dosage group), and 200 mg/kg (high-dosage group) of the present composition for 7 and 14 days, respectively.
Figure 3:
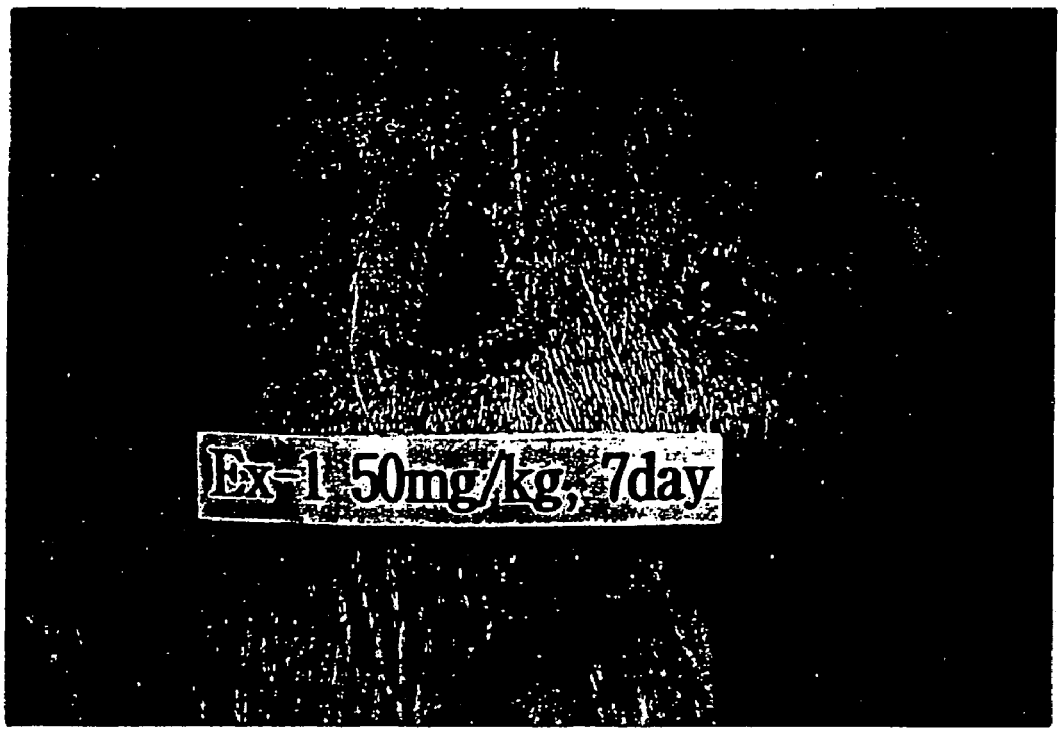
Figure 4:
Figure 5:
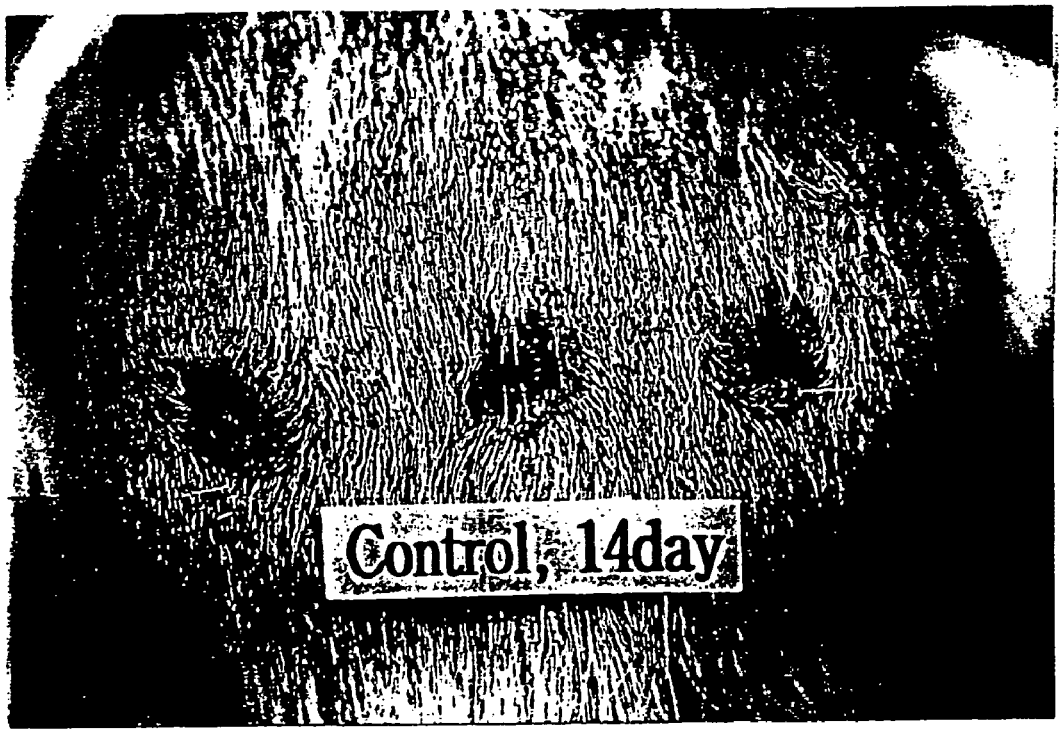
Figure 6:
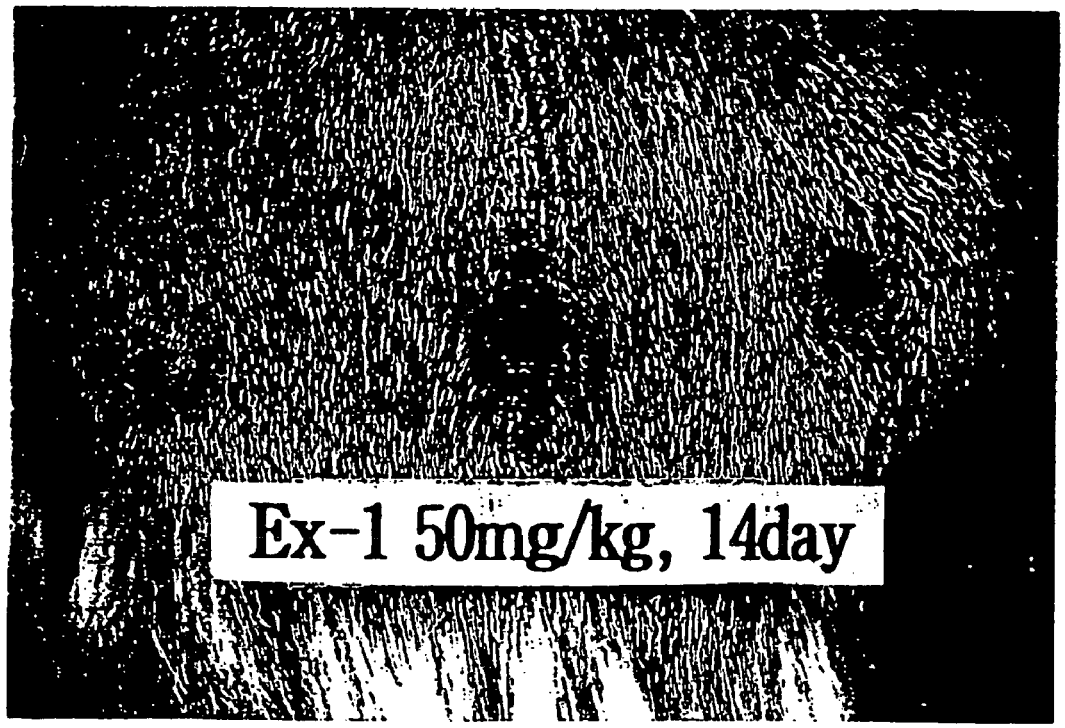
Figure 7:
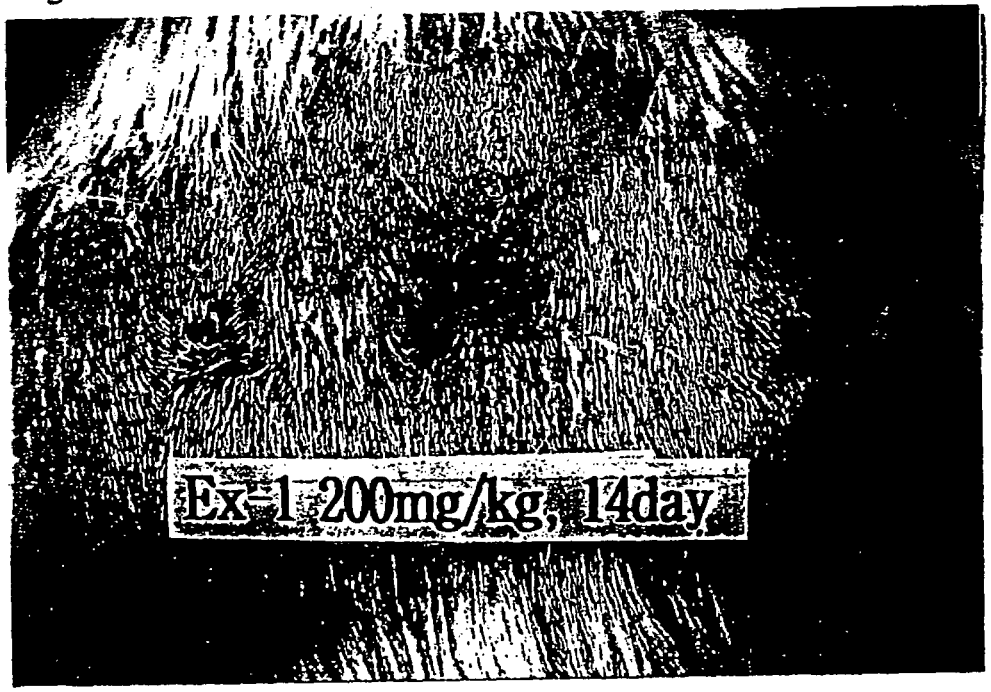
Figure 8:
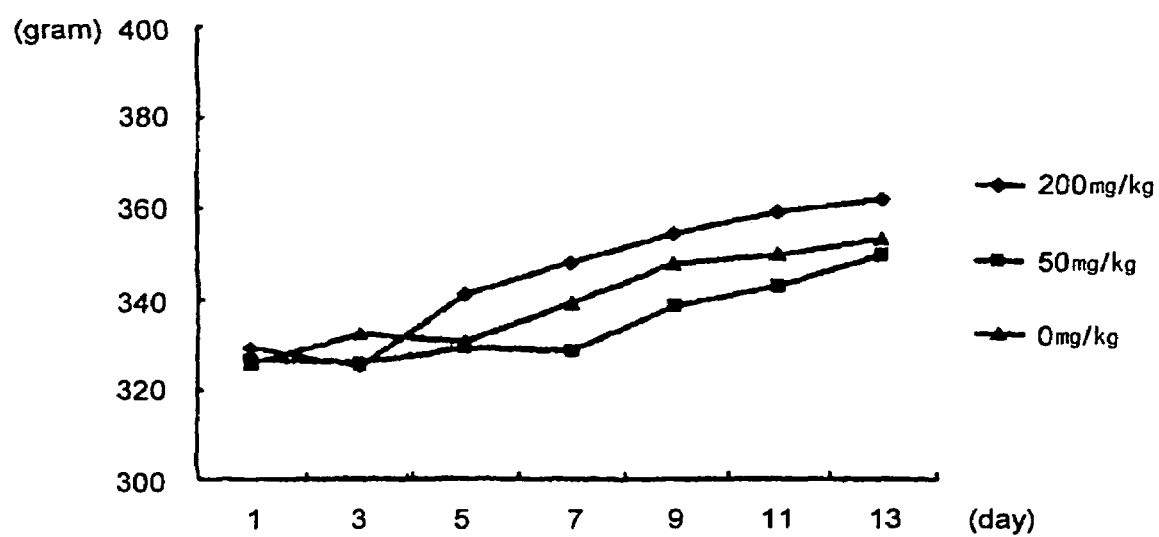
FIG. 8 is a graph showing changes in body weights of rats in control and experimental groups.

As a result, at 7 days after inducing wounds, degrees of contraction and healing of wound were observed to be higher in the high-dosage group (FIG. 4) than in the control group (FIG. 2), and degree of wound healing was high on both ends in the case of the low-dosage group (FIG. 3). At 14 days after inducing wounds, a more noticeable healing effect was observed in the high-dosage group (FIG. 7) than in the control group (FIG. 5), and the higher healing effect was also observed in the low-dosage group (FIG. 6) than in the control group, even though it was lower than in the high-dosage group. For changes of body weights for 14 days, it was observed that body weights slightly decreased because of stress and pain after inducing wounds, but there was no significant difference in body weights between the groups during the whole experiments (FIG. 8).

Figure 9:
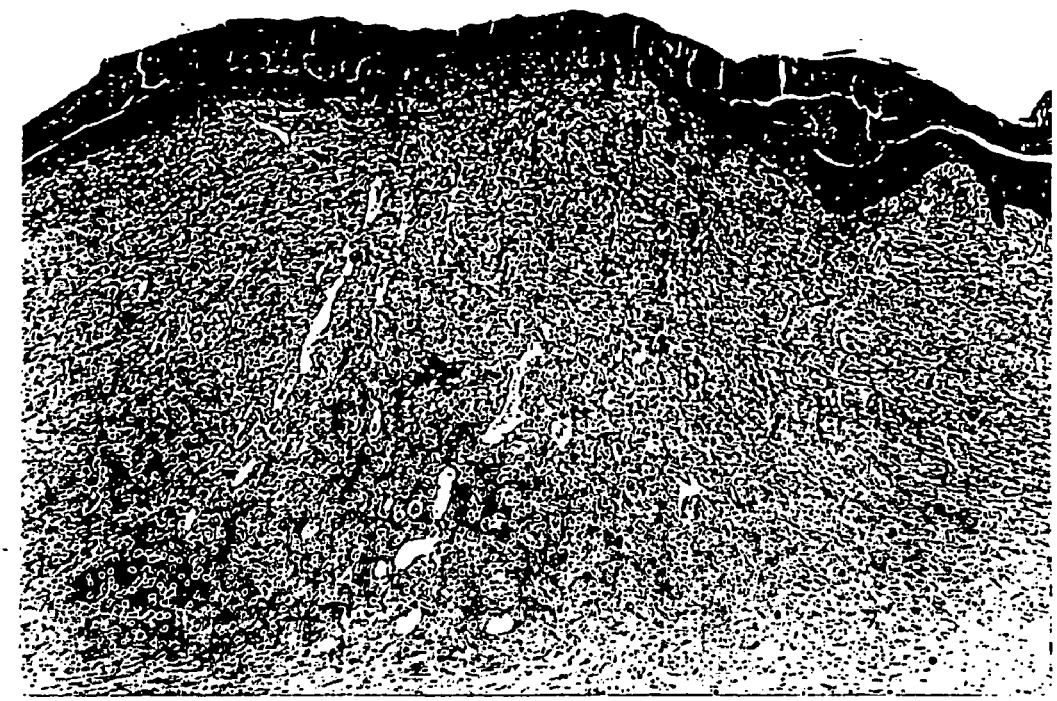
FIGS. 9 to 14 are optical micrographs showing the H&E-stained wound tissues in control and experimental groups.
Figure 10:
Figure 11:
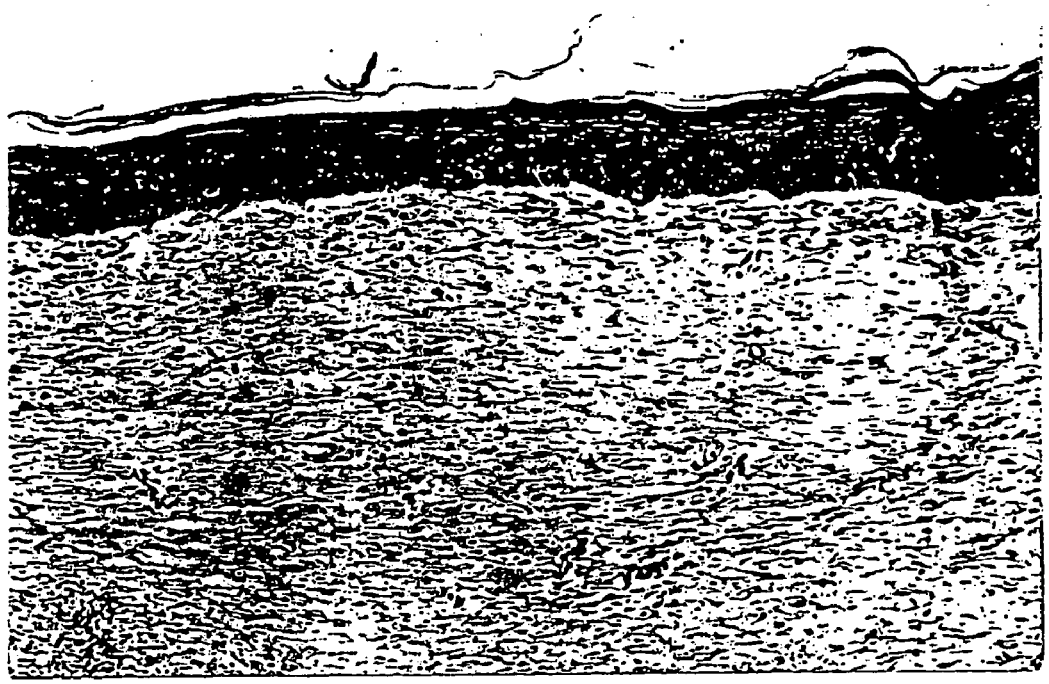
Figure 12:
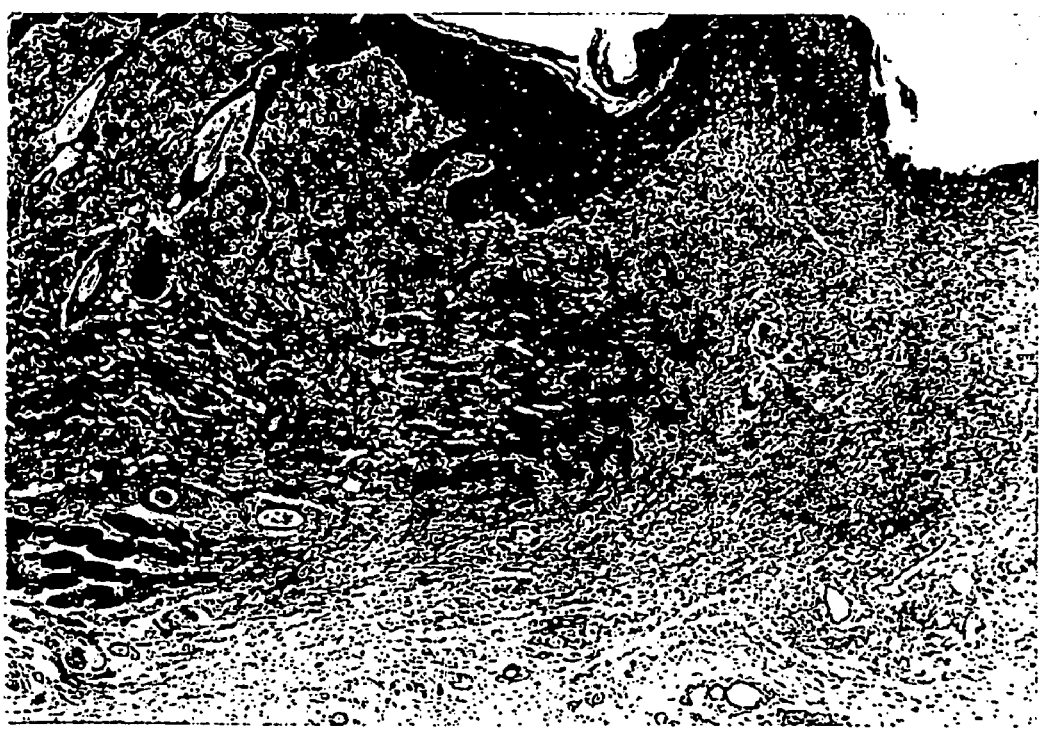
Figure 13:
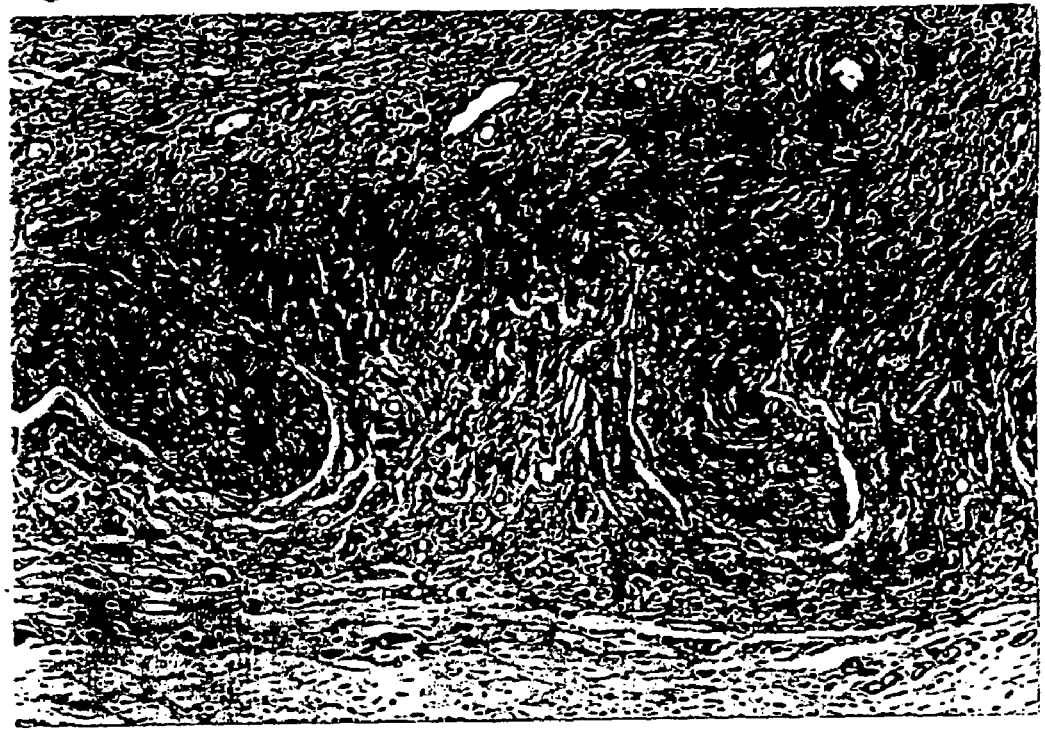
Figure 14:
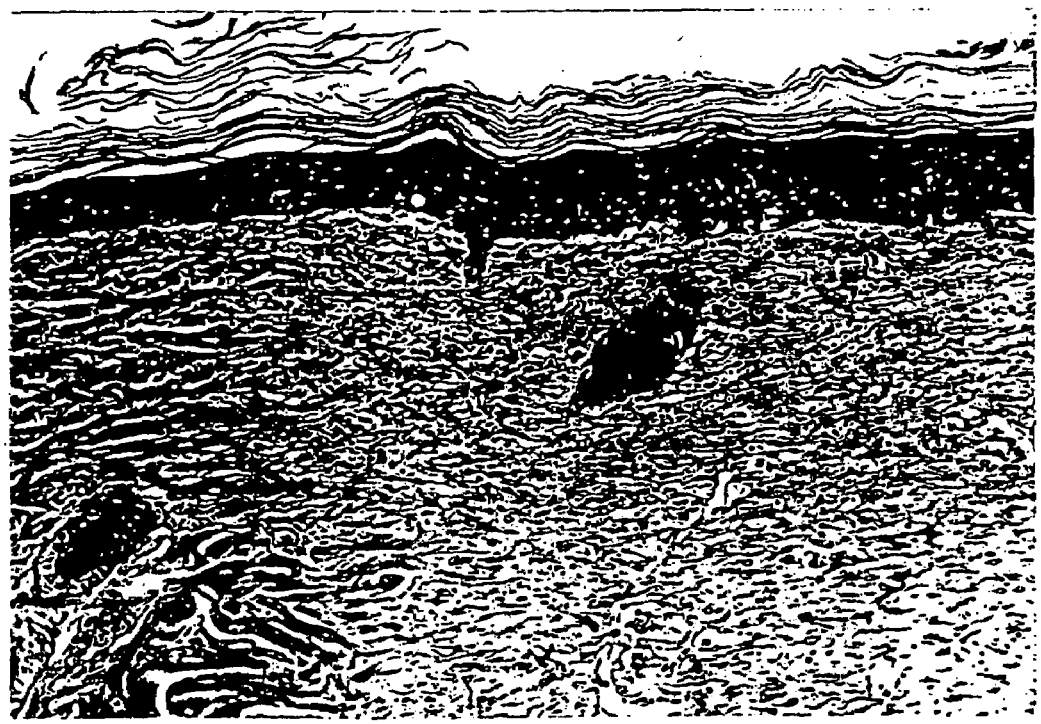

At 14 days after inducing wounds, the wound tissues in the control and experimental groups were made into specimens and the specimens were stained with H&E and observed under an optical microscope. In the control group (FIGS. 9 and 10), thin epithelial layer, sparse tissue texture, and low distribution of vessels were observed. On the contrary, in the low-dosage group (FIGS. 11 and 12), thicker epithelial layer and denser tissue texture than the control group were observed. In the high-dosage group, smoother epithelial surface than in other groups, slowly curved epithelial layer, and sweat gland and hair follicles were observed (FIGS. 13 and 14). Usually, sweat gland and hair follicles could be observed at 28 days after injury, but hair follicles could be observed in most high-dosage groups and some low-dosage groups, which means that the wound healing effect of the composition of the present invention was very fast. Therefore, the present composition was demonstrated to have a fast wound healing effect upon oral administration.

EXPERIMENT 2

Evaluation of Fracture-healing Effect

1. Healing Process of Bone Fracture

The healing process of bone fracture is a very complex one including normal wound healing processes, which leads to restoration of original integrity and strength which can stand against the loading of skeleton through normal physiological processes. The healing processes of bone fracture may be divided into the following three phases:

First phase: Inflammatory phase wherein an inflammatory reaction is triggered by formation of hematoma that is a mass of blood clot from blood leaked out of injured vessels in a fractured area, followed by acute edema;

Second phase: Reconstructive phase wherein fibroblast proliferation and granulation tissue formation with angiogenesis induce tissue organization, which leads to progressive endochondral ossification through formation of cartilage and callus (immature bone tissue) around fractured sites; and, Third phase: Remodeling phase wherein a newly formed callus is gradually replaced by a mature lamellar bone and an excessively formed bone is absorbed by osteoclasts.

In this experiment, in order to examine a fracture-healing effect of the composition of the present invention, the healing index of bone fracture was evaluated with a bone fracture model in rats.

2. Methods

After the fibular fracture was surgically induced in rats, the composition obtained from Example 1 was administered with changing doses for six weeks.

That is, after fifteen adult male rats (318±40 g) were intraperitoneally injected with 15 mg/100 of ketamine HCl to induce general anesthesia, the rat's hairs were shaven in the right hind leg with an electric clipper, and the rats were laid on the left side, and disinfected at the surgical area with povidon-iodine and alcohol. After skin incision, anterior tibia muscle and gastrocnemius muscle were dissected bluntly and the fibula was exposed. The exposed fibula was forced with a clamp to induce the transverse fracture. Then, the fifteen rats with fibular fracture were divided into three groups, five rats per group, and the composition of the present invention was orally administered at 100 mg/kg body weight (1st group), 50 mg/kg body weight (2nd group) and 0 mg/kg body weight (control group) as the freeze-dried powder, respectively.

The healing process of bone fracture was radiologically examined at 1, 2, 3, 4 and 5 weeks after inducing bone fracture, and, at the final week, the locomotion amount was measured and compared between the groups by performing the rota-rod test at 8 rpm, and the rats were autopsied for the subsequent histopathological examination.

3. Results

As an index of fracture healing effect, gross examination, radiography, histomorphological examination of callus, and rota-rod test for tissues of the fractured sites were performed.

(1) Changes in Body Weights

Figure 15:
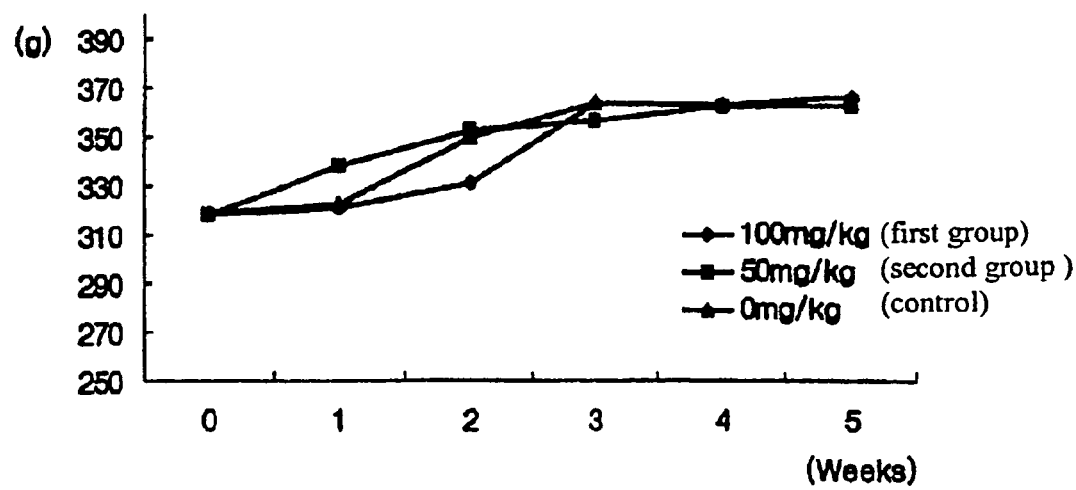
FIG. 15 is a graph showing changes in body weights after orally administering 0 mg/kg (control), 50 mg/kg (first group), and 100 mg/kg (second group) of the present composition for 6 weeks, respectively.

Body weights were measured once a week, and during the whole experiments, there was no significant difference in body weights compared with the control group (FIG. 15).

(2) Radiological Examination

Radiographs were taken at 1, 2, 3, 4, and 5 weeks after inducing bone fracture to observe healing of the right fibular fracture. The results are shown in FIGS. 16 to 25.

Figure 16:
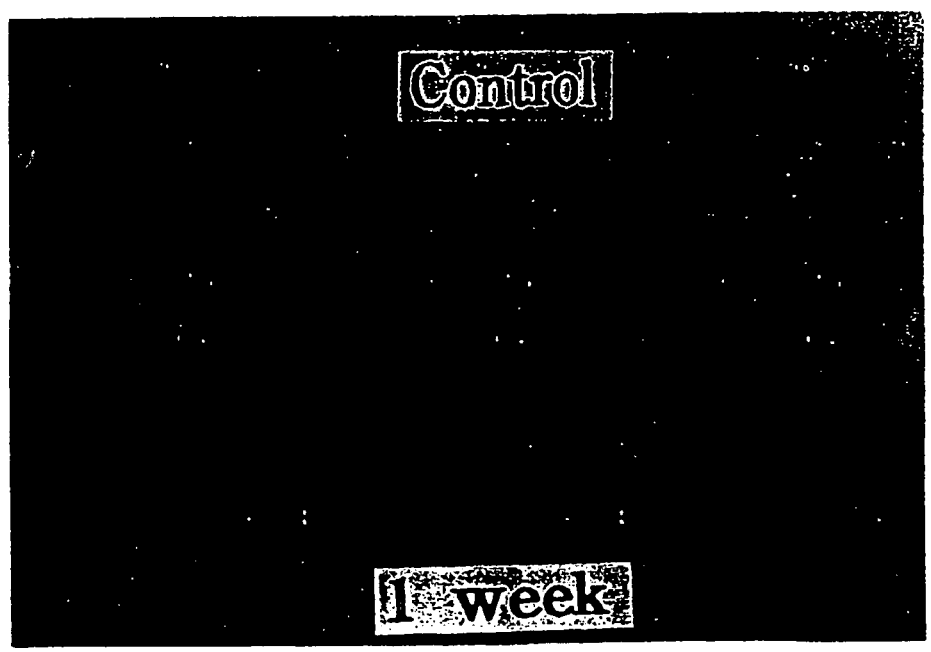
FIGS. 16 to 25 are radiographs of the fractured sites in control and first group.
Figure 17:
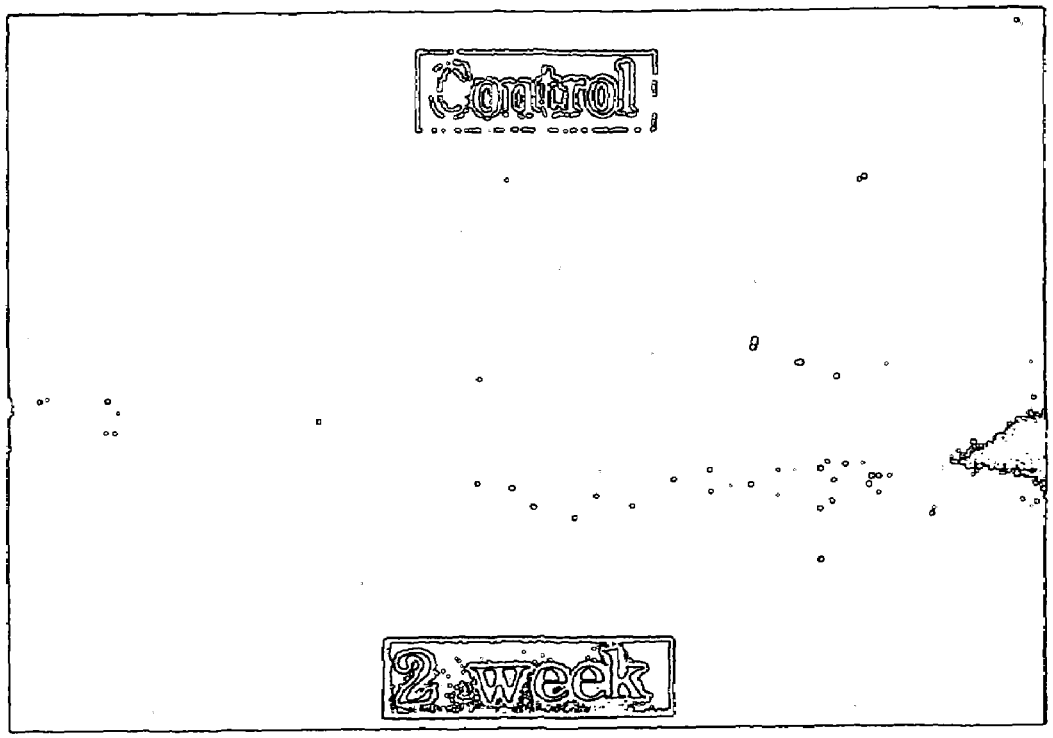
Figure 18:
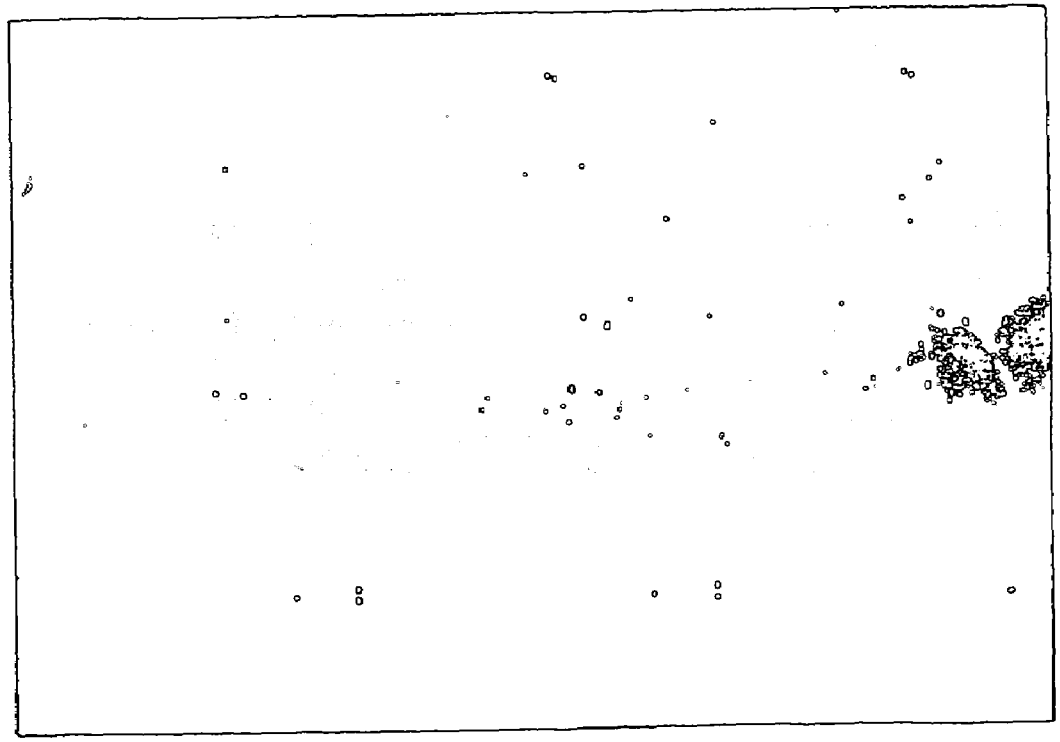
Figure 19:
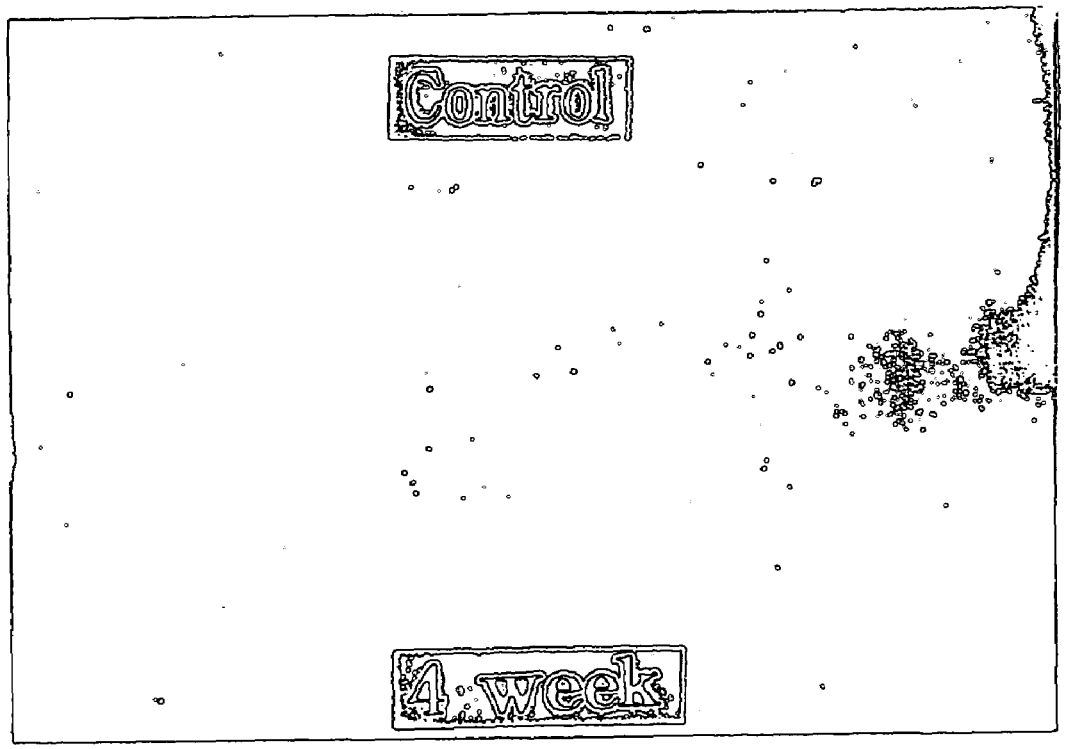
Figure 20:
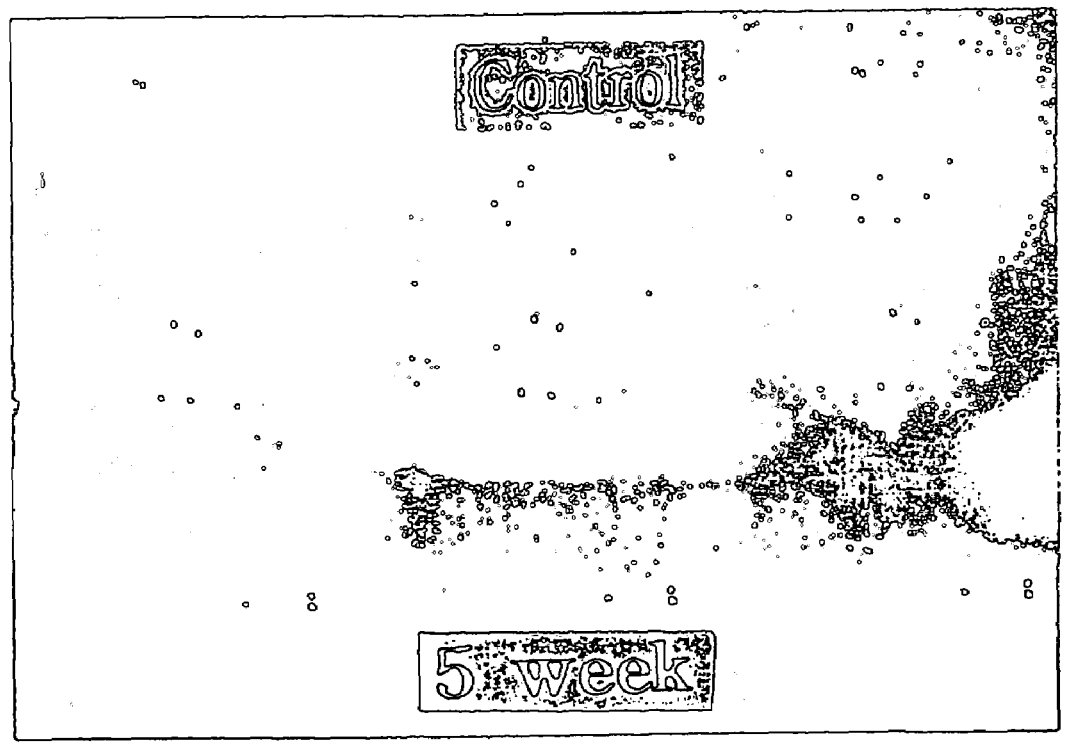
Figure 21:
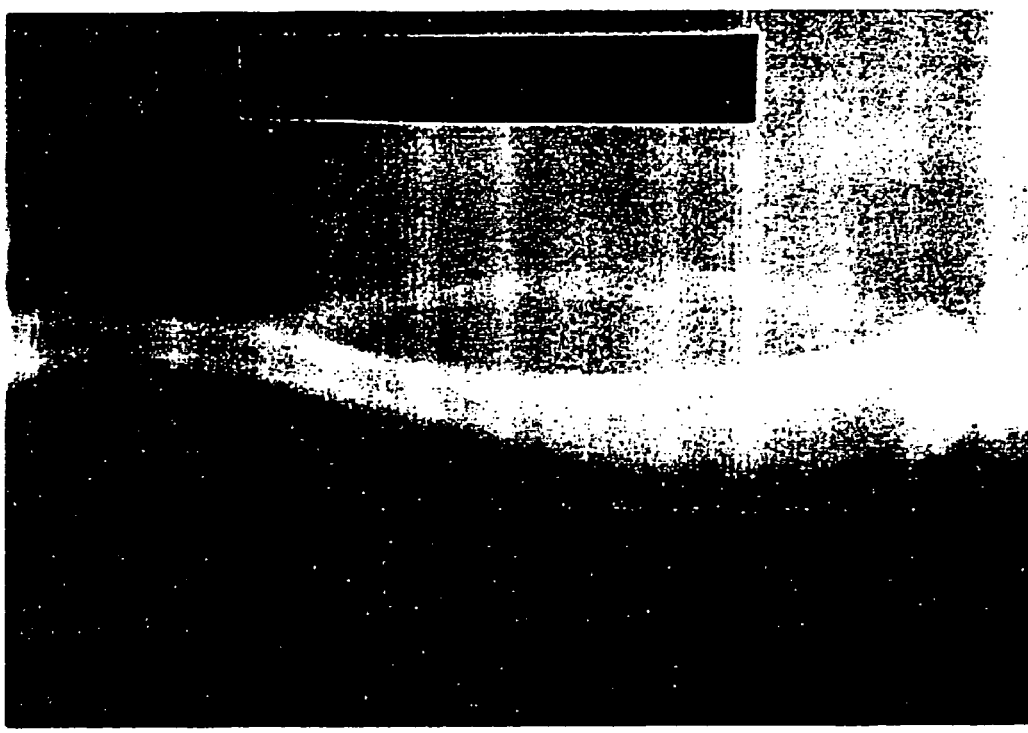
Figure 22:
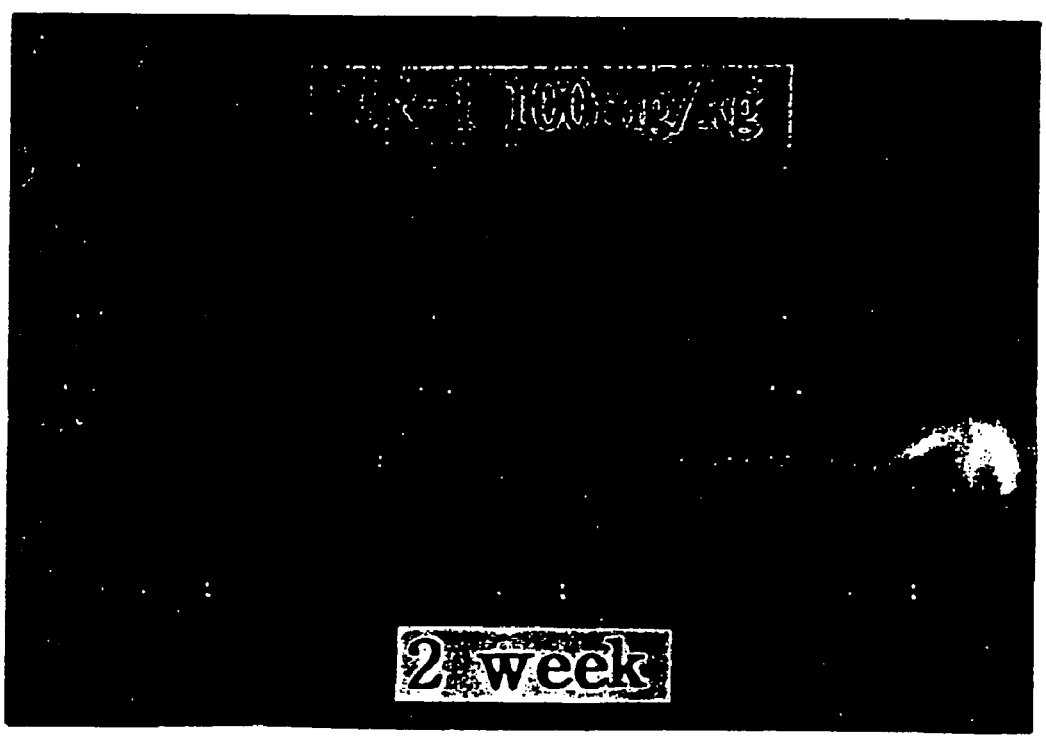
Figure 23:
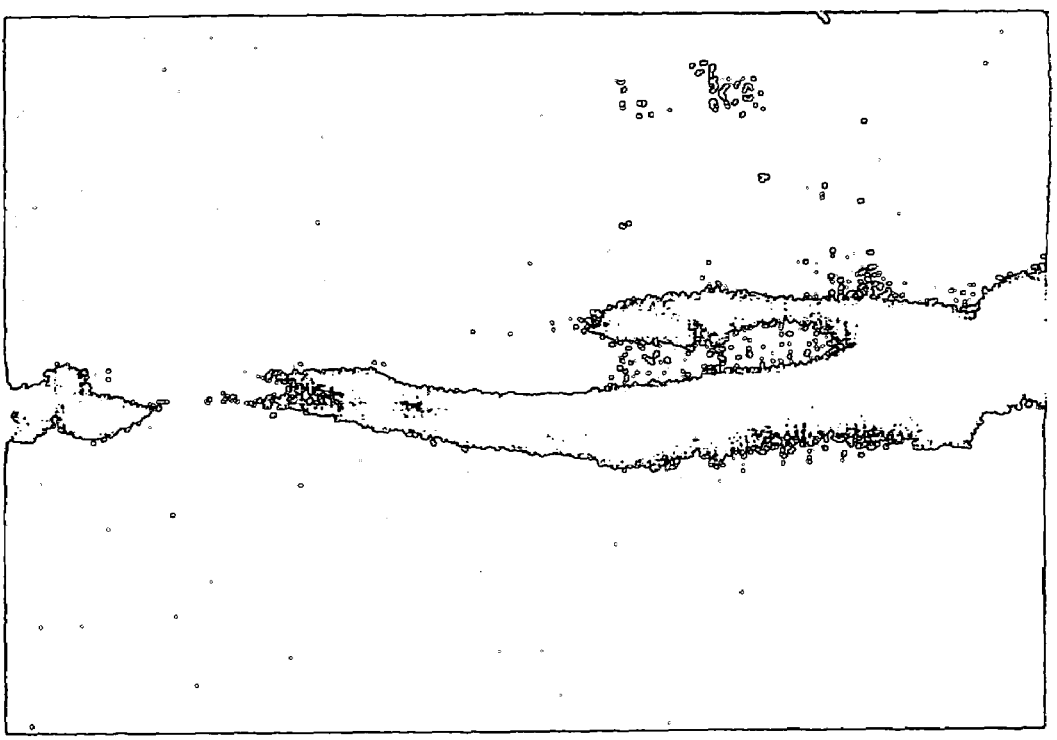
Figure 24:
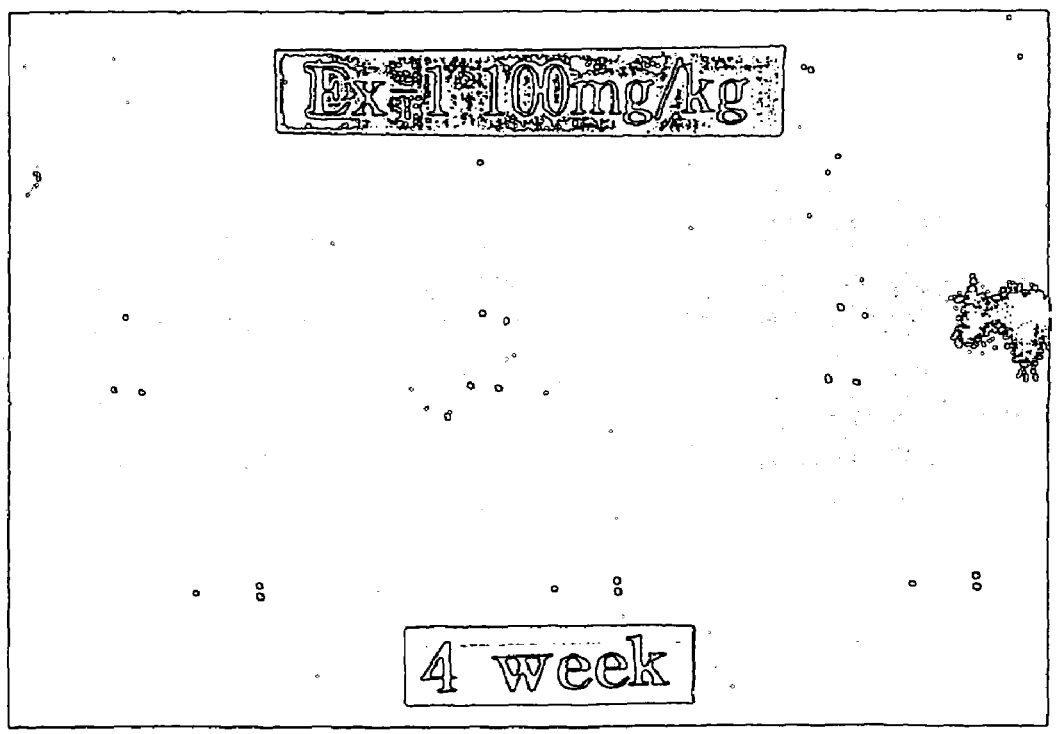
Figure 25:
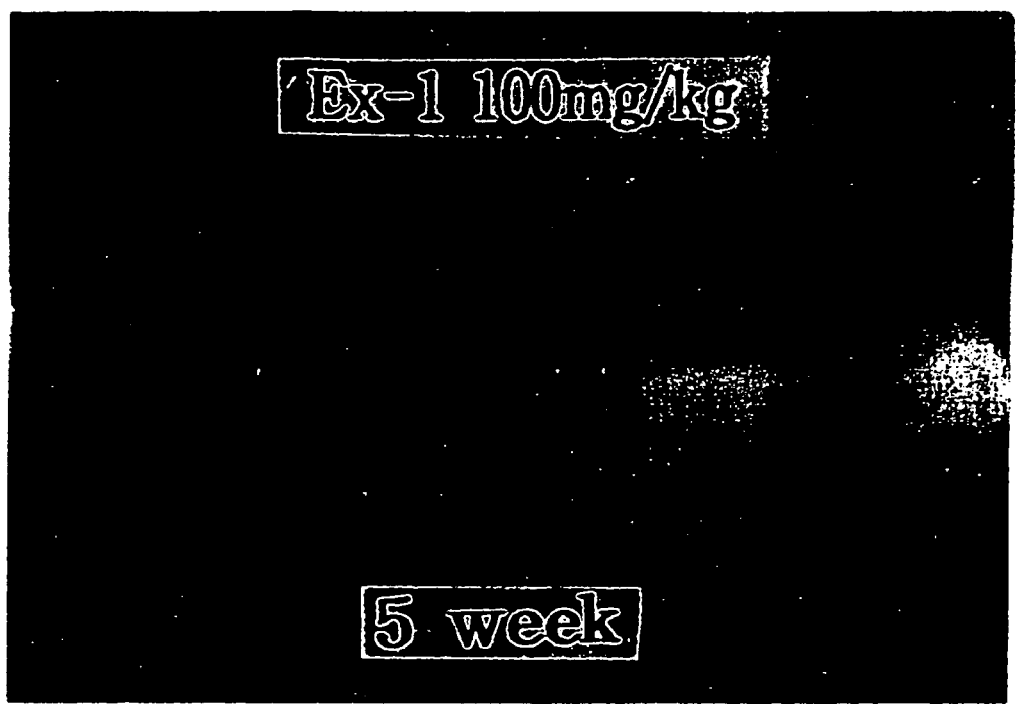

Radiographs taken at one week after fracture did not show any significant difference between control and drug administered groups (FIGS. 16 and 21). On radiographs taken at 3 weeks after fracture, however, significant differences were shown between the groups and they were in proportion to administered doses. The healing speed in the first group was faster than that in control group by about one week and the healing speed in the second group was about as half fast as that in the first group. On the final radiograph taken at 5 weeks after fracture, complete calcification was observed in the first group (FIG. 25), while only callus formation and incomplete calcification were observed in the control group (FIG. 20).

(3) Rota-rod Test

Figure 26:
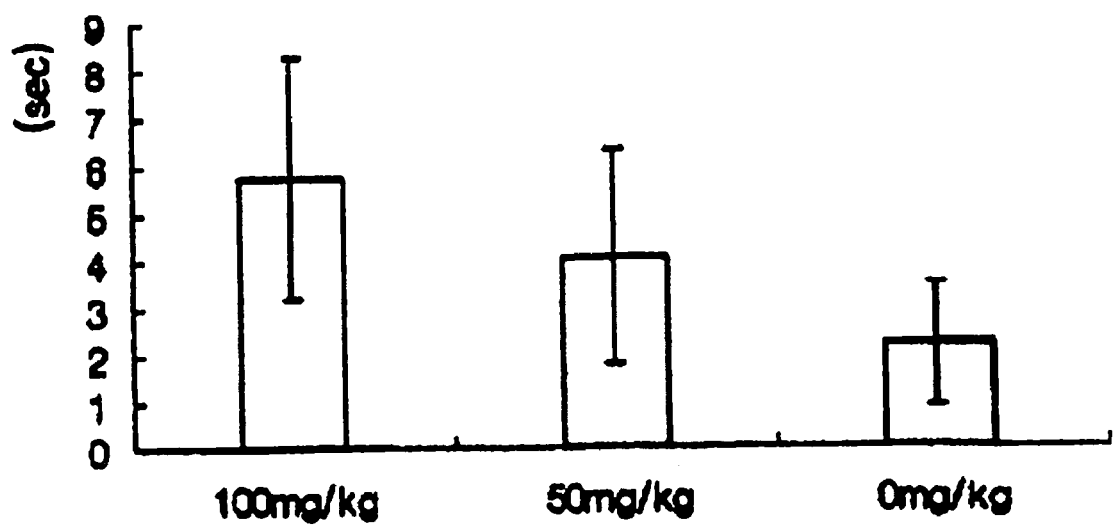
FIG. 26 is a graph showing the endurance time in a rota-rod test after administering the present composition for 5 weeks.

In order to indirectly examine the degree of fracture healing in the trial groups before autopsy at 5 weeks, locomotion ability was evaluated. Individual animals in all the trial groups were placed on a rota-rod and the endurance time was measured, and the results are shown in FIG. 26. It shows that the first group had the longest endurance time.

(4) Gross Examination after Extraction of Bone

Figure 27:
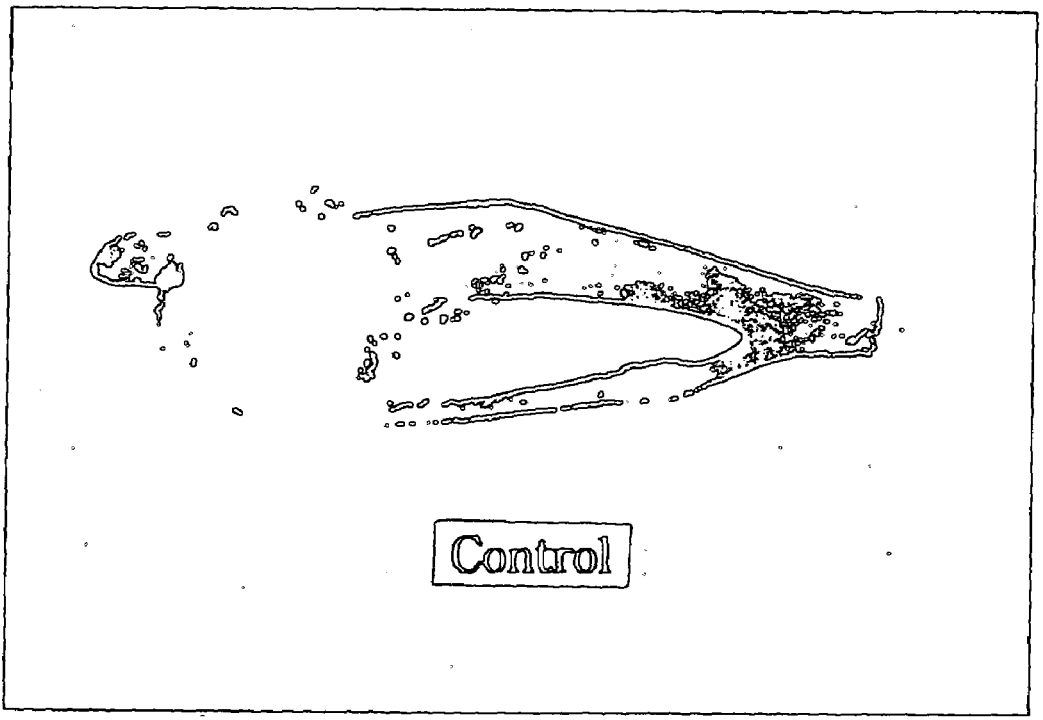
FIGS. 27 to 29 are photographs showing the gross examination results of the extracted tibia and fibula in control, first, and second groups; and, FIGS. 30 to 32 are photographs showing the examination results of the fibular tissues in control, first, and second groups.
Figure 28:
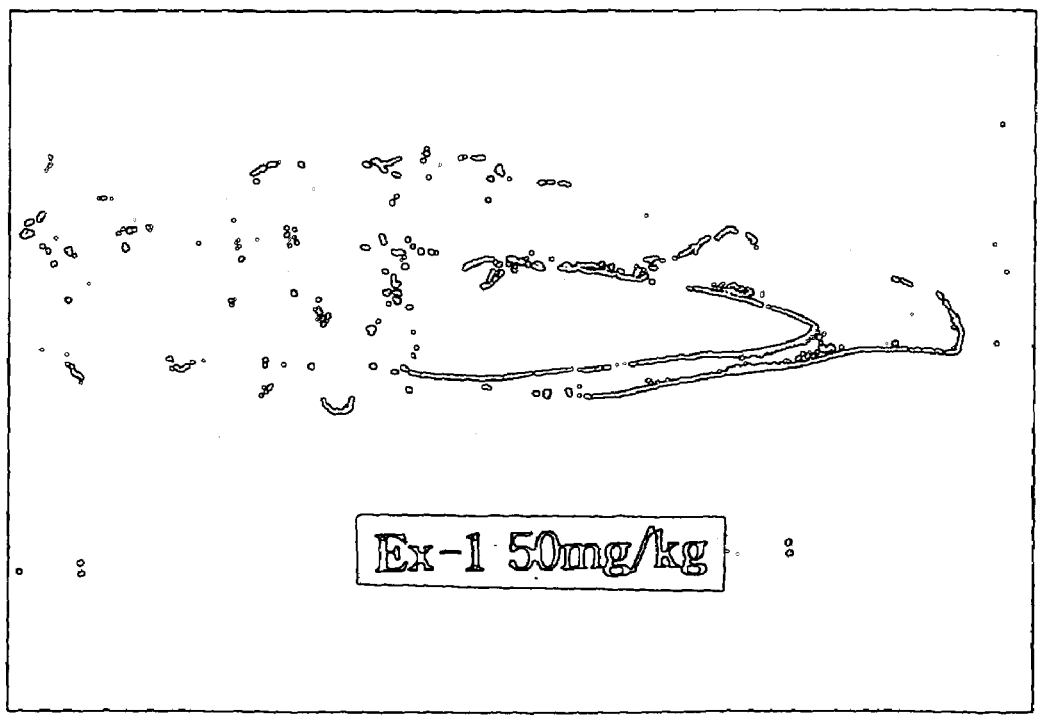
Figure 29:
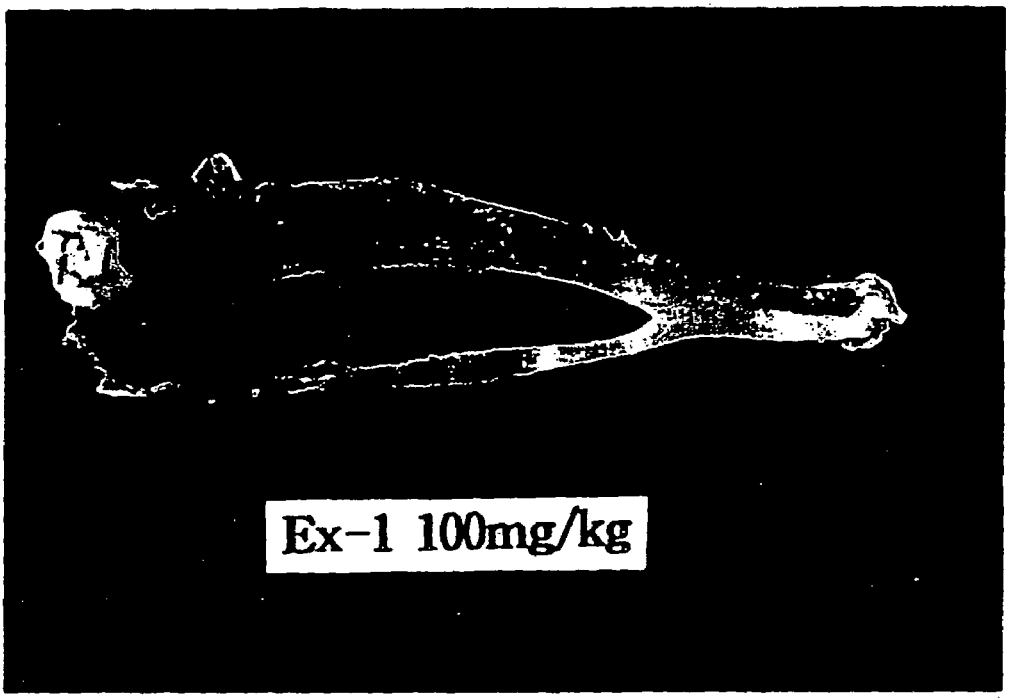

The extracted tibia and fibula from autopsies were examined with the naked eyes. Healing process seemed to be in remodeling phase after completing the formation of callus in the low-dosage group (FIG. 28) and the final step of remodeling phase in the high-dosage group (FIG. 29), while the callus was actively formed in the control group at five weeks (FIG. 27).

(5) Histopathological Examination

Figure 30:
Figure 31:
Figure 32:

A histopathological examination was performed after decalcifying the extracted fibula and making specimen. Ossification seemed to progress by mineral deposition in the low-dosage group (FIG. 31) and restoration of normal bone tissues by reconstruction (remodeling) was observed in the high-dosage group (FIG. 32), while only the callus was formed and lacunar structures were clearly observed in the control group (FIG. 30).

4. Conclusion

From the above results, the composition of the present invention was concluded to have a fast healing effect on bone fracture upon oral administration.

INDUSTRIAL APPLICABILITY

As can be seen from the above experiments, the extract composition of the present invention having the healing effect for injuries, particularly, wound or bone fracture is extremely useful as a pharmaceutical composition for healing injuries, or a health food or an animal feed for post-surgical recovery of human beings or animals.

What is claimed is:

1. A method for treating a subject suffering from an injury comprising administering to the subject an effective amount of an extract composition obtainable by extracting Astragali Radix, Ginseng Radix, Carthami Flos, Angelicae Gigantis Radix, Cnidii Rhizoma, Rehmanniae Radix Preparata, Paeoniae Radix and Cinnamomi Cortex Spissus with water while heating.

2. The method of claim 1 wherein the subject is suffering from a wound.

3. The method of claim 1 wherein the subject has suffered a bone fracture.

4. The method of claim 1 wherein the subject has undergone surgery.

5. The method of claim 1 wherein the subject is a human.

6. The method of claim 1 wherein the composition is obtainable by further mixing one or more herbal medicines selected from the group consisting of Atractylodis Rhizoma alba, Hoelen, Aurantii Nobilis Pericarpium, Glycyrrhizae Radix, Eucommiae Cortex, Myrrh, Amomi Semen, Walnut, Zingiberis Rhizoma, and Zizyphi Fructus, and extracting the mixture with water while heating.

7. The method of claim 1 wherein the weight ratio of Astragali Radix, Ginseng Radix, Carthami Flos, Angelicae Gigantis Radix, Cnidii Rhizoma, Rehmanniae Radix Preparata, Paeoniae Radix, and Cinnamomi Cortex Spissus is 4–20:2–12:2–12:2–12:2–12:2–12:2–12:2–12.

8. The method of claim 1 wherein the weight ratio of Astragali Radix, Ginseng Radix, Carthami Flos, Angelicae Gigantis Radix, Cnidii Rhizoma, Rehmanniae Radix Preparata, Paeoniae Radix and Cinnamomi Cortex Spissus is 8–16:4–8:4–8:4–8:4–8:4–8:4–8:4–8.

9. The method of claim 1 wherein the composition is obtainable by further mixing one or more herbal medicines selected from the group consisting of 2–12 parts of Atractylodis Rhizoma alba, 2–12 parts of Hoelen, 2–10 parts of Aurantii Nobilis Pericarpium, 2–12 parts of Glycyrrhizae Radix, 2–18 parts of Eucommiae Cortex, 2–8 parts of Myrrh, 2–12 parts of Amomi Semen, 4–20 parts of Walnut, 2–10 parts of Zingiberis Rhizoma, and 2–10 parts of Zizyphi Fructus, and extracting the whole mixture with water while heating.

10. The method of claim 1 wherein the composition is obtainable by further mixing one or more herbal medicines selected from the group consisting of 4–8 parts of Atractylodis Rhizoma alba, 4–8 parts of Hoelen, 3–8 parts of Aurantil Nobilis Pericarpium, 4–8 parts of Glycyrrhizae Radix, 4–10 parts of Eucommiae Cortex, 2–6 parts of Myrrh, 4–8 parts of Amomi Semen, 6–15 parts of Walnut, 3–8 parts of Zingiberis Rhizoma, and 3–8 parts of Zizyphi Fructus, and extracting the whole mixture with water while heating.

* * * * *